US012708632B2

(12) United States Patent
Checketts et al.

(10) Patent No.: US 12,708,632 B2
(45) Date of Patent: Aug. 18, 2026

(54) USE OF CANNABIDIOL IN THE TREATMENT OF SEIZURES ASSOCIATED WITH RARE EPILEPSY SYNDROMES RELATED TO STRUCTURAL ABNORMALITIES OF THE BRAIN

(71) Applicant: Jazz Pharmaceuticals Research UK Limited, Sittingbourne (GB)

(72) Inventors: Daniel Adam Checketts, Sittingbourne (GB); Kevin James Craig, Sittingbourne (GB)

(73) Assignee: Jazz Pharmaceuticals Research UK Limited, Sittingbourne (GB)

( * ) Notice: Subject to any disclaimer, the term of this patent is extended or adjusted under 35 U.S.C. 154(b) by 700 days.

(21) Appl. No.: 18/006,129

(22) PCT Filed: Jul. 15, 2021

(86) PCT No.: PCT/EP2021/069782
§ 371 (c)(1),
(2) Date: Jan. 19, 2023

(87) PCT Pub. No.: WO2022/017909
PCT Pub. Date: Jan. 27, 2022

(65) Prior Publication Data

US 2023/0285428 A1 Sep. 14, 2023

(30) Foreign Application Priority Data

Jul. 20, 2020 (GB) .................................... 2011120

(51) Int. Cl.

| | |
|---|---|
| ***A61K 31/00*** | (2006.01) |
| ***A61K 31/165*** | (2006.01) |
| ***A61K 31/19*** | (2006.01) |
| ***A61K 31/197*** | (2006.01) |
| ***A61K 31/36*** | (2006.01) |
| ***A61K 31/4015*** | (2006.01) |
| ***A61K 31/4192*** | (2006.01) |
| ***A61K 31/423*** | (2006.01) |
| ***A61K 31/53*** | (2006.01) |
| ***A61K 31/5513*** | (2006.01) |
| ***A61P 25/08*** | (2006.01) |

(52) U.S. Cl.
CPC .......... *A61K 31/658* (2023.05); *A61K 31/165* (2013.01); *A61K 31/19* (2013.01); *A61K 31/197* (2013.01); *A61K 31/36* (2013.01); *A61K 31/4015* (2013.01); *A61K 31/4192* (2013.01); *A61K 31/423* (2013.01); *A61K 31/53* (2013.01); *A61K 31/5513* (2013.01); *A61P 25/08* (2018.01)

(58) Field of Classification Search
CPC .. A61K 2300/00; A61K 31/05; A61K 31/165; A61K 31/19; A61K 31/197; A61K 31/36; A61K 31/4015; A61K 31/4192; A61K 31/423; A61K 31/53; A61K 31/551; A61K 31/5513; A61K 31/658; A61K 31/7048; A61K 45/06; A61P 25/08
See application file for complete search history.

(56) References Cited

U.S. PATENT DOCUMENTS

| | | | |
|---|---|---|---|
| 8,632,825 | B2 | 1/2014 | Velasco Diez et al. |
| 8,790,719 | B2 | 7/2014 | Parolaro et al. |
| 9,017,737 | B2 | 4/2015 | Kikuchi et al. |
| 9,125,859 | B2 | 9/2015 | Whalley et al. |
| 9,474,726 | B2 | 10/2016 | Guy et al. |
| 9,675,654 | B2 | 6/2017 | Parolaro et al. |
| 9,949,936 | B2 | 4/2018 | Guy et al. |
| 9,949,937 | B2 | 4/2018 | Guy et al. |
| 9,956,183 | B2 | 5/2018 | Guy et al. |
| 9,956,184 | B2 | 5/2018 | Guy et al. |
| 9,956,185 | B2 | 5/2018 | Guy et al. |
| 9,956,186 | B2 | 5/2018 | Guy et al. |
| 9,962,341 | B2 | 5/2018 | Stott et al. |
| 10,039,724 | B2 | 8/2018 | Stott et al. |
| 10,092,525 | B2 | 10/2018 | Guy et al. |
| 10,098,867 | B2 | 10/2018 | Javid et al. |
| 10,111,840 | B2 | 10/2018 | Guy et al. |
| 10,137,095 | B2 | 11/2018 | Guy et al. |
| 10,220,005 | B2 | 3/2019 | Martinez-Orgado et al. |
| 10,226,433 | B2 | 3/2019 | Di Marzo et al. |

(Continued)

FOREIGN PATENT DOCUMENTS

| | | | | |
|---|---|---|---|---|
| WO | WO-2011001169 A1 | | 1/2011 | |
| WO | WO-2019071302 A1 | * | 4/2019 | ........... A61K 31/192 |
| WO | WO-2019207319 A1 | | 10/2019 | |

OTHER PUBLICATIONS

Aitken, V., "Desperate mum saved epileptic son's life by smuggling cannabis oil into Scotland," Daily Record, Jul. 19, 2019, https://www.dailyrecord.co.uk/news/health/brave-scots-mum-saved-epileptic-18342434, 16 pages.
[Author Unknown], "Mum wins fight for cannabis oil treatment for severely epileptic son," Glasgow Live, Jan. 16, 2019, https://www.glasgowlive.co.uk/news/health/mum-wins-fight-cannabis-oil-15686500, 20 pages.
Caraballo, R. et al., "Effectiveness of cannabidiol in a prospective cohort of children with drug resistant epileptic encephalopathy in Argentina," Seizure: European Journal of Epilepsy, 80:75-80 (2020).
Crippa, J. A. S. et al., "Δ9-THC Intoxication by Cannabidiol-Enriched Cannabis Extract in Two Children with Refractory Epilepsy: Full Remission after Switching to Purified Cannabidiol," Front Pharmacol., 7: 359 (2016); Published online Sep. 30, 2016. doi: 10.3389/fphar.2016.00359, 6 pages.

(Continued)

*Primary Examiner* — Savitha M Rao
(74) *Attorney, Agent, or Firm* — COOLEY LLP

(57) ABSTRACT

The present invention relates to the use of cannabidiol (CBD) for the treatment of seizures associated with rare epilepsy syndromes. In particular the seizures associated with rare epilepsy syndromes that are treated are experienced in patients diagnosed with Cortical Dysplasia and Cortical Brain Malformation. In a further embodiment the types of seizures include atonic, tonic, and focal without impairment seizures. Preferably the dose of CBD is between 5 mg/kg/day to 50 mg/kg/day.

13 Claims, No Drawings

(56) References Cited

U.S. PATENT DOCUMENTS 10,583,096 B2 3/2020 Guy et al.
10,603,288 B2 3/2020 Guy et al.
10,653,641 B2 5/2020 Robson et al.
10,709,671 B2 7/2020 Guy et al.
10,709,673 B2 7/2020 Guy
10,709,674 B2 7/2020 Guy et al.
10,729,665 B2 8/2020 Whalley et al.
10,758,514 B2 9/2020 Liu et al.
10,765,643 B2 9/2020 Guy et al.
10,799,467 B2 10/2020 Whalley et al.
10,807,777 B2 10/2020 Whittle
10,849,860 B2 12/2020 Guy et al.
10,918,608 B2 2/2021 Guy et al.
10,966,939 B2 4/2021 Guy et al.
11,000,486 B2 5/2021 Wright et al.
11,065,209 B2 7/2021 Guy et al.
11,065,227 B2 7/2021 Stott et al.
11,096,905 B2 8/2021 Guy et al.
11,147,776 B2 10/2021 Stott et al.
11,147,783 B2 10/2021 Stott et al.
11,154,516 B2 10/2021 Guy et al.
11,154,517 B2 10/2021 Guy et al.
11,160,757 B1 11/2021 Wilkhu et al.
11,160,795 B2 11/2021 Guy et al.
11,207,292 B2 12/2021 Guy et al.
11,229,612 B2 1/2022 Wright et al.
11,291,631 B2 4/2022 Shah
11,311,498 B2 4/2022 Guy et al.
11,318,109 B2 5/2022 Whalley et al.
11,357,741 B2 6/2022 Guy et al.
11,400,055 B2 8/2022 Guy et al.
11,406,623 B2 8/2022 Guy et al.
11,413,266 B2 8/2022 Biró et al.
11,419,829 B2 8/2022 Whalley et al.
11,426,362 B2 8/2022 Wright et al.
11,446,258 B2 9/2022 Guy et al.
11,590,087 B2 2/2023 Guy et al.
11,633,369 B2 4/2023 Guy et al.
11,679,087 B2 6/2023 Guy et al.
11,684,598 B2 6/2023 Stott et al.
11,701,330 B2 7/2023 Guy et al.
2015/0359756 A1 12/2015 Guy et al.
2017/0239193 A1 8/2017 Guy et al.
2018/0071210 A1 3/2018 Wilkhu et al.
2018/0228751 A1 8/2018 Stott et al.
2019/0167583 A1 6/2019 Shah
2019/0314296 A1 10/2019 Wright et al.
2019/0321307 A1 10/2019 Guy et al.
2019/0365667 A1 12/2019 Wright et al.
2020/0138738 A1 5/2020 Guy et al.
2020/0179303 A1 6/2020 Guy et al.
2020/0206153 A1 7/2020 Whalley et al.
2020/0237683 A1 7/2020 Whalley et al.
2020/0297656 A1 9/2020 Guy et al.
2020/0352878 A1 11/2020 Guy et al.
2021/0015789 A1 1/2021 Guy et al.
2021/0052512 A1 2/2021 Guy et al.
2021/0059949 A1 3/2021 Wilkhu et al.
2021/0059960 A1 3/2021 Wilkhu et al.
2021/0059976 A1 3/2021 Wilkhu et al.
2021/0069333 A1 3/2021 Velasco Diez et al.
2021/0100755 A1 4/2021 Whalley et al.
2021/0169824 A1 6/2021 Guy et al.
2021/0177773 A1 6/2021 Guy et al.
2021/0290565 A1 9/2021 Guy et al.
2021/0308072 A1 10/2021 Wright et al.
2021/0330636 A1 10/2021 Guy et al.
2021/0401771 A1 12/2021 Guy et al.
2022/0000800 A1 1/2022 Guy et al.
2022/0008355 A1 1/2022 Guy et al.
2022/0016048 A1 1/2022 Guy et al.
2022/0023232 A1 1/2022 Guy et al.
2022/0040155 A1 2/2022 Guy et al.
2022/0062197 A1 3/2022 Stott et al.
2022/0062211 A1 3/2022 Stott et al.
2022/0087951 A1 3/2022 Knappertz
2022/0096397 A1 3/2022 Wright et al.
2022/0168266 A1 6/2022 Guy et al.
2022/0183997 A1 6/2022 Guy et al.
2022/0184000 A1 6/2022 Guy et al.
2022/0202738 A1 6/2022 Guy et al.
2022/0211629 A1 7/2022 Wilkhu et al.
2022/0226257 A1 7/2022 Guy et al.
2022/0233495 A1 7/2022 Silcock et al.
2022/0249396 A1 8/2022 Guy et al.
2022/0257529 A1 8/2022 Guy et al.
2022/0265573 A1 8/2022 Guy et al.
2022/0288055 A1 9/2022 Silcock et al.
2022/0378715 A1 12/2022 Guy et al.
2022/0378738 A1 12/2022 Guy et al.
2022/0387347 A1 12/2022 Whalley et al.
2022/0395470 A1 12/2022 Whalley et al.
2022/0395471 A1 12/2022 Guy et al.
2023/0000789 A1 1/2023 Guy et al.
2023/0022487 A1 1/2023 Guy et al.
2023/0024312 A1 1/2023 Whalley et al.
2023/0026079 A1 1/2023 Guy et al.
2023/0032502 A1 2/2023 Guy et al.
2023/0038423 A1 2/2023 Silcock et al.
2023/0068885 A1 3/2023 Guy et al.
2023/0143812 A1 5/2023 Knappertz et al.
2023/0235825 A1 7/2023 Thompson et al.
2023/0248664 A1 8/2023 Guy
2023/0263744 A1 8/2023 Guy et al.

OTHER PUBLICATIONS

Eadie, M. J., "Shortcomings in the current treatment of epilepsy," Expert Rev Neurother., 12(12):1419-1427 (2012).

Elsohly, M. & Gul, W., Handbook of Cannabis, Chapter 1, Constituents of Cannabis Sativa, Roger Pertwee, Ed., 2012, 21 pages.

Epidiolex® (cannabidiol) oral solution, CV, Prescribing Information, 2018, 30 pages; https://www.accessdata.fda.gov/drugsatfda_docs/label/2018/210365lbl.pdf.

García-Rincón, D. et al., "Contribution of Altered Endocannabinoid System to Overactive mTORC1 Signaling in Focal Cortical Dysplasia," Front. Pharmacol., 9:1508 (2019); doi: 10.3389/fphar.2018.01508, 13 pages.

Gedde, M. G., "Clinical Experience with Cannabis in Treatment-Resistant Pediatric Epilepsy," Marijuana for Medical Professionals Health Conference, Sep. 9-11, 2014; https://pediatriccannabissupport.com/images/gedde_presentation.pdf, 45 pages.

Jeffay, J., "Save My Beautiful Son' Lanarkshire lad, 6, who suffers 10 seizures a Night from epilepsy—refused medical cannabis as he doesn't qualify," The Scottish Sun, Nov. 4, 2018, https://www.thescottishsun.co.uk/news/3441326/lanarkshire-lad-cole-thomson-epilepsy-medical-cannabis/, 8 pages.

Kabat, J. & Król, P., "Focal cortical dysplasia—review," Pol J Radiol, 77(2):35-43 (2012).

Kwan, P. et al., "Definition of drug resistant epilepsy: consensus proposal by the ad hoc Task Force of the ILAE Commission on Therapeutic Strategies," Epilepsia, 51(6):1069-1077; doi:10.1111/j.1528-1167.2009.02397.x. Epub Nov. 3, 2009. Erratum in: Epilepsia. Sep. 2010; 51(9):1922.

Lambrou, A., "Cannabis campaign mum fears 'miracle' treatment has come too late to cure East Kilbride boy's stroke-like seizures," Daily Record, Feb. 21, 2019, https://www.dailyrecord.co.uk/news/local-news/cannabis-campaign-mum-fears-miracle-14021236, 21 pages.

Lambrou, A., "East Kilbride mum's desperate plea for cannabis to save her severely epileptic son," Daily Record, Nov. 15, 2018, https//www.dailyrecord.co.uk/news/local-news/east-kilbride-mums-desperate-plea-13584906, 10 pages.

Lambrou, A., "We did it': Family overjoyed at cannabis oil win for severely epileptic East Kilbride boy," Daily Record News, Jan. 16, 2019, https://www.dailyrecord.co.uk/news/local-news/we-it-family-overjoyed-cannabis-13859745, 13 pages.

Laux, L. C. et al., "Long-term safety and efficacy of cannabidiol in children and adults with treatment resistant Lennox-Gastaut syn-

(56) References Cited

OTHER PUBLICATIONS drome or Dravet syndrome: Expanded access program results," Epilepsy Research, 154:13-20 (2019).
Lazarini-Lopes, W. et al., "The anticonvulsant effects of cannabidiol in experimental models of epileptic seizures: From behavior and mechanisms to clinical insights," Neuroscience and Biobehavioral Reviews, 111:166-182 (2020).
Leventer, R. J. et al., "Malformations of cortical development and epilepsy," Dialogues Clin Neurosci., 10:47-62 (2008).
Longley, R., "Arizona Superior Court Helps 5-Year-Old Zander Welton With Cannabis Extract Ruling," Medical Jane, retrieved on Aug. 16, 2023, https://www.medicaljane.com/2014/03/24/arizona-supreme-court-helps-5-year-old-zander-welton-with-cannabis-extract-ruling/#, 3 pages.
Mohney, G., "Parents File Suit to Allow Son to Take Marijuana Extract," ABC News, Nov. 1, 2013, https://abcnews.go.com/Health/parents-file-suit-son-medicinal-marijuana-extract/story?id=20740614, 5 pages.
Pertwee, R. G., "The Pharmacology and Therapeutic Potential of Cannabidiol," Cannabinoids, Chapter 3, DiMarzo, V. (Ed.), pp. 32-83 (2004).
Sulak, D. et al., "The current status of artisanal cannabis for the treatment of epilepsy in the United States," Epilepsy & Behavior, 70:328-333 (2017).
Szaflarski, J. P. et al., "Long-term safety and treatment effects of cannabidiol in children and adults with treatment-resistant epilepsies: Expanded access program results," Epilepsia, 59:1540-1548 (2018).
Thurman, D. J. et al., "Standards for epidemiologic studies and surveillance of epilepsy," Epilepsia, 52 (Suppl 7):2-26 (2011).
U.S. Appl. No. 15/640,033, filed Jun. 30, 2017.
U.S. Appl. No. 16/768,241, filed May 29, 2020.
U.S. Appl. No. 16/959,350, filed Jun. 30, 2020.
U.S. Appl. No. 16/959,354, filed Jun. 30, 2020.
U.S. Appl. No. 16/959,357, filed Jun. 30, 2020.
U.S. Appl. No. 16/935,005, filed Jul. 21, 2020.
U.S. Appl. No. 17/012,448, filed Sep. 4, 2020.
U.S. Appl. No. 17/050,956, filed Oct. 27, 2020.
U.S. Appl. No. 17/102,109, filed Nov. 23, 2020.
U.S. Appl. No. 17/231,625, filed Apr. 15, 2021.
U.S. Appl. No. 17/296,066, filed May 21, 2021.
U.S. Appl. No. 17/296,076, filed May 21, 2021.
U.S. Appl. No. 17/424,682, filed Jul. 21, 2021.
U.S. Appl. No. 17/426,442, filed Jul. 28, 2021.
U.S. Appl. No. 17/406,401, filed Aug. 19, 2021.
U.S. Appl. No. 17/435,892, filed Sep. 2, 2021.
U.S. Appl. No. 17/472,000, filed Sep. 10, 2021.
U.S. Appl. No. 17/548,232, filed Dec. 10, 2021.
U.S. Appl. No. 17/606,370, filed Oct. 25, 2021.
U.S. Appl. No. 17/611,824, filed Nov. 16, 2021.
U.S. Appl. No. 17/529,005, filed Nov. 17, 2021.
U.S. Appl. No. 17/615,422, filed Nov. 30, 2021.
U.S. Appl. No. 17/552,487, filed Dec. 16, 2021.
U.S. Appl. No. 17/576,868, filed Jan. 14, 2022.
U.S. Appl. No. 17/585,485, filed Jan. 26, 2022.
U.S. Appl. No. 17/627,946, filed Jan. 18, 2022.
U.S. Appl. No. 17/631,069, filed Jan. 28, 2022.
U.S. Appl. No. 17/638,629, filed Feb. 25, 2022.
U.S. Appl. No. 17/689,607, filed Mar. 8, 2022.
U.S. Appl. No. 17/689,245, filed Mar. 8, 2022.
U.S. Appl. No. 17/744,224, filed May 13, 2022.
U.S. Appl. No. 17/705,443, filed Mar. 28, 2022.
U.S. Appl. No. 17/768,048, filed Apr. 11, 2022.
U.S. Appl. No. 17/770,435, filed Apr. 20, 2022.
U.S. Appl. No. 17/770,436, filed Apr. 20, 2022.
U.S. Appl. No. 17/771,184, filed Apr. 22, 2022.
U.S. Appl. No. 17/771,190, filed Apr. 22, 2022.
U.S. Appl. No. 17/771,195, filed Apr. 22, 2022.
U.S. Appl. No. 17/771,183, filed Apr. 22, 2022.
U.S. Appl. No. 17/777,734, filed May 18, 2022.
U.S. Appl. No. 17/777,677, filed May 18, 2022.
U.S. Appl. No. 17/777,681, filed May 18, 2022.
U.S. Appl. No. 17/841,167, filed Jun. 15, 2022.
U.S. Appl. No. 17/786,949, filed Jun. 17, 2022.
U.S. Appl. No. 17/817,753, filed Aug. 5, 2022.
U.S. Appl. No. 17/853,367, filed Jun. 29, 2022.
U.S. Appl. No. 18/002,437, filed Dec. 19, 2022.
U.S. Appl. No. 18/005,838, filed Jan. 17, 2023.
U.S. Appl. No. 18/005,841, filed Jan. 17, 2023.
U.S. Appl. No. 18/005,845, filed Jan. 17, 2023.
U.S. Appl. No. 18/005,843, filed Jan. 17, 2023.
U.S. Appl. No. 18/005,847, filed Jan. 17, 2023.
U.S. Appl. No. 18/005,848, filed Jan. 17, 2023.
U.S. Appl. No. 18/005,851, filed Jan. 18, 2023.
U.S. Appl. No. 18/005,852, filed Jan. 18, 2023.
U.S. Appl. No. 18/005,853, filed Jan. 18, 2023.
U.S. Appl. No. 18/005,959, filed Jan. 18, 2023.
U.S. Appl. No. 18/005,960, filed Jan. 18, 2023.
U.S. Appl. No. 18/005,961, filed Jan. 18, 2023.
U.S. Appl. No. 18/006,125, filed Jan. 19, 2023.
U.S. Appl. No. 18/006,127, filed Jan. 19, 2023.
U.S. Appl. No. 18/006,131, filed Jan. 19, 2023.
U.S. Appl. No. 18/006,133, filed Jan. 19, 2023.
U.S. Appl. No. 18/006,121, filed Jan. 19, 2023.
U.S. Appl. No. 18/161,603, filed Jan. 30, 2023.
U.S. Appl. No. 18/170,235, filed Feb. 16, 2023.
U.S. Appl. No. 18/043,810, filed Mar. 2, 2023.
U.S. Appl. No. 18/044,941, filed Mar. 10, 2023.
U.S. Appl. No. 18/245,856, filed Mar. 17, 2023.
U.S. Appl. No. 18/186,792, filed Mar. 20, 2023.
U.S. Appl. No. 18/311,221, filed May 2, 2023.
U.S. Appl. No. 18/320,906, filed May 19, 2023.
U.S. Appl. No. 18/256,307, filed Jun. 7, 2023.
U.S. Appl. No. 18/257,373, filed Jun. 14, 2023.
U.S. Appl. No. 18/257,537, filed Jun. 14, 2023.
U.S. Appl. No. 18/257,479, filed Jun. 14, 2023.
U.S. Appl. No. 18/258,485, filed Jun. 20, 2023.
U.S. Appl. No. 18/446,405, filed Aug. 8, 2023.
U.S. Appl. No. 18/546,254, filed Aug. 11, 2023.

* cited by examiner

USE OF CANNABIDIOL IN THE TREATMENT OF SEIZURES ASSOCIATED WITH RARE EPILEPSY SYNDROMES RELATED TO STRUCTURAL ABNORMALITIES OF THE BRAIN

CROSS-REFERENCE TO RELATED APPLICATIONS

This application is a U.S. National Phase application, filed under 35 U.S.C. § 371(c), of International Application No. PCT/EP2021/069782, filed Jul. 15, 2021, which claims priority to, and the benefit of, United Kingdom Patent Application No. 2011120.9, filed Jul. 20, 2020. Each of these documents is incorporated by reference herein in its entirety for all purposes.

FIELD OF THE INVENTION

The present invention relates to the use of cannabidiol (CBD) for the treatment of seizures associated with rare epilepsy syndromes. In particular the seizures associated with rare epilepsy syndromes that are treated are experienced in patients diagnosed with Cortical Dysplasia and Cortical Brain Malformation. In a further embodiment the types of seizures include atonic, tonic, and focal without impairment seizures. Preferably the dose of CBD is between 5 mg/kg/day to 50 mg/kg/day.

In a further embodiment the CBD used is in the form of a highly purified extract of *cannabis* such that the CBD is present at greater than 95% of the total extract (w/w) and the cannabinoid tetrahydrocannabinol (THC) has been substantially removed, to a level of not more than 0.15% (w/w).

Preferably the CBD used is in the form of a botanically derived purified CBD which comprises greater than or equal to 98% (w/w) CBD and less than or equal to 2% (w/w) of other cannabinoids. More preferably the other cannabinoids present are THC at a concentration of less than or equal to 0.1% (w/w); CBD-C1 at a concentration of less than or equal to 0.15% (w/w); CBDV at a concentration of less than or equal to 0.8% (w/w); and CBD-C4 at a concentration of less than or equal to 0.4% (w/w). The botanically derived purified CBD preferably also comprises a mixture of both trans-THC and cis-THC. Alternatively, a synthetically produced CBD is used.

Most preferably the other cannabinoids present are THC at a concentration of about 0.01% to about 0.1% (w/w); CBD-C1 at a concentration of about 0.1% to about 0.15% (w/w); CBDV at a concentration of about 0.2% to about 0.8% (w/w); and CBD-C4 at a concentration of about 0.3% to about 0.4% (w/w). Most preferably still the THC is present at a concentration of about 0.02% to about 0.05% (w/w).

Where the CBD is given concomitantly with one or more other anti-epileptic drugs (AED), the CBD may be formulated for administration separately, sequentially or simultaneously with one or more AED or the combination may be provided in a single dosage form.

BACKGROUND TO THE INVENTION

Epilepsy occurs in approximately 1% of the population worldwide, (Thurman et al., 2011) of which 70% are able to adequately control their symptoms with the available existing anti-epileptic drugs (AED). However, 30% of this patient group, (Eadie et al., 2012), are unable to obtain seizure freedom from the AED that are available and as such are termed as suffering from intractable or “treatment-resistant epilepsy” (TRE).

Intractable or treatment-resistant epilepsy was defined in 2009 by the International League Against Epilepsy (ILAE) as “failure of adequate trials of two tolerated and appropriately chosen and used AED schedules (whether as monotherapies or in combination) to achieve sustained seizure freedom” (Kwan et al., 2009).

Individuals who develop epilepsy during the first few years of life are often difficult to treat and as such are often termed treatment resistant. Children who undergo frequent seizures in childhood are often left with neurological damage which can cause cognitive, behavioral and motor delays.

Childhood epilepsy is a relatively common neurological disorder in children and young adults with a prevalence of approximately 700 per 100,000. This is twice the number of epileptic adults per population.

When a child or young adult presents with a seizure, investigations are normally undertaken in order to investigate the cause. Childhood epilepsy can be caused by many different syndromes and genetic mutations and as such diagnosis for these children may take some time.

The main symptom of epilepsy is repeated seizures. In order to determine the type of epilepsy or the epileptic syndrome that a patient is suffering from an investigation into the type of seizures that the patient is experiencing is undertaken. Clinical observations and electroencephalography (EEG) tests are conducted and the type(s) of seizures are classified according to the ILEA classification.

Generalized seizures, where the seizure arises within and rapidly engages bilaterally distributed networks, can be split into six subtypes: tonic-clonic (grand mal) seizures; absence (petit mal) seizures; clonic seizures; tonic seizures; atonic seizures and myoclonic seizures.

Focal (partial) seizures where the seizure originates within networks limited to only one hemisphere, are also split into sub-categories. Here the seizure is characterized according to one or more features of the seizure, including aura, motor, autonomic and awareness/responsiveness. Where a seizure begins as a localized seizure and rapidly evolves to be distributed within bilateral networks this seizure is known as a bilateral convulsive seizure, which is the proposed terminology to replace secondary generalized seizures (generalized seizures that have evolved from focal seizures and are no longer remain localized).

Focal seizures where the subject's awareness/responsiveness is altered are referred to as focal seizures with impairment and focal seizures where the awareness or responsiveness of the subject is not impaired are referred to as focal seizures without impairment.

Cortical brain malformation, also known as Malformations of Cortical Development (MCD), is the most common cause of medically refractory epilepsy in the pediatric population and the second/third most common etiology of medically intractable seizures in adults[1]. MCD encompass a wide spectrum of disorders with various underlying genetic etiologies and clinical manifestations. They are brain malformations that result from abnormalities affecting the normal processes of cortical development and involve cells that under normal circumstances would participate in formation of the cerebral cortex[2]. They are often associated with recurrent seizures which are difficult to control and arise as a consequence of either malpositioning of normal cortical neurons or the presence of abnormal cortical neurons.

Cortical dysplasia is a malformation of cortical development. Both genetic and acquired factors are involved in the pathogenesis of cortical dysplasia.

In general, three types of cortical dysplasia are recognized[1]. Type I focal cortical dysplasia with mild symptomatic expression and late onset, is more often seen in adults, with changes present in the temporal lobe. Clinical symptoms are more severe in type II of cortical dysplasia usually seen in children. In this type, more extensive changes occur outside the temporal lobe with predilection for the frontal lobes. Type III includes one of the above-described dysplasias with damage in another part of the brain e.g. hippocampal sclerosis, tumor, vascular malformation or acquired pathology during early life.

Anticonvulsants are a first line treatment in cortical dysplasia. If anticonvulsants fail to control seizure activity, neurosurgery may be required to remove or disconnect the abnormal cells from the rest of the brain. Neurosurgery can range from removing an entire hemisphere, a small lesionectomy, or multiple transsections to try to disconnect the abnormal tissue from the rest of the brain.

Cannabidiol (CBD), a non-psychoactive derivative from the *cannabis* plant, has demonstrated anti-convulsant properties in several anecdotal reports, pre-clinical and clinical studies both in animal models and humans. Three randomized control trials showed efficacy of the purified pharmaceutical formulation of CBD in patients with Dravet and Lennox-Gastaut syndrome.

Based on these three trials, a botanically derived purified CBD preparation was approved by FDA in June 2018 for the treatment of seizures associated with Dravet and Lennox-Gastaut syndromes.

In 2019 a Scottish newspaper reported the treatment of a child with cortical dysplasia using CBD medication[3]. There is no mention of the types of seizures experienced by the patient.

Garcia-Rincón et al. (2019)[4] attempted to characterize the possible contribution of endocannabinoid system signaling to focal cortical dysplasia. They found that an altered endocannabinoid system contributes to increased activity of a protein signaling pathway, the mammalian target of rapamycin complex 1 (mTORC1) pathway, which is itself associated with some malformations of cortical development such as focal cortical dysplasia.

Szaflarski et al. (2018)[5] and Laux et al. (2019)[6] disclose the use of CBD to treat epileptic syndromes including Lennox-Gastaut Syndrome and Dravet Syndrome. Cortical malformation and dysplasia are listed in a list of several etiologies included in the patient cohort.

However, it is not disclosed what types of seizures these patients experienced and indeed whether treatment was effective in reducing their seizures.

Crippa et al (2016)[7] discloses the use of a cannabinoid treatment containing no THC to treat a girl with focal cortical dysplasia. There is no mention of the types of seizures experienced by the patient. Further disclosures in the form of news articles[8,9] refer to a patient with cortical dysplasia treated with CBD. Again, there is no disclosure of seizure types suffered by the patient.

The applicant has found by way of an open label, expanded-access program that treatment with CBD resulted in a significant reduction in atonic, tonic and focal without impairment seizures in patients with Cortical Dysplasia and Cortical Brain Malformation.

BRIEF SUMMARY OF THE DISCLOSURE

In accordance with a first aspect of the present invention there is provided a cannabidiol (CBD) preparation for use in the treatment of seizures associated with Cortical Dysplasia and Cortical Brain Malformation.

In a further embodiment the seizures associated with Cortical Dysplasia and Cortical Brain Malformation are atonic, tonic and focal without impairment seizures.

In a further embodiment, the CBD preparation comprises greater than 95% (w/w) CBD and not more than 0.15% (w/w) tetrahydrocannabinol (THC).

Preferably the CBD preparation comprises greater than or equal to 98% (w/w) CBD and less than or equal to 2% (w/w) other cannabinoids, wherein the less than or equal to 2% (w/w) other cannabinoids comprise the cannabinoids tetrahydrocannabinol (THC); cannabidiol-C1 (CBD-C1); cannabidivarin (CBDV); and cannabidiol-C4 (CBD-C4), and wherein the THC is present as a mixture of trans-THC and cis-THC.

Preferably the CBD preparation is used in combination with one or more concomitant anti-epileptic drugs (AED).

Preferably the one or more AED is selected from the group consisting of: valproic acid, levetiracetam, clobazam, vigabatrin, zonisamide, rufinamide, lacosamide, topiramate and lamotrigine. More preferably the AED is clobazam.

In one embodiment the CBD is present is isolated from *cannabis* plant material. Preferably at least a portion of at least one of the cannabinoids present in the CBD preparation is isolated from *cannabis* plant material.

In a further embodiment the CBD is present as a synthetic preparation. Preferably at least a portion of at least one of the cannabinoids present in the CBD preparation is prepared synthetically.

Preferably the dose of CBD is greater than 5 mg/kg/day. More preferably the dose of CBD is 20 mg/kg/day. More preferably the dose of CBD is 25 mg/kg/day. More preferably the dose of CBD is 50 mg/kg/day.

In accordance with a second aspect of the present invention there is provided a method of treating seizures associated with Cortical Dysplasia and Cortical Brain Malformation comprising administering a cannabidiol (CBD) preparation to the subject in need thereof.

Definitions

Definitions of some of the terms used to describe the invention are detailed below:

Over 100 different cannabinoids have been identified, see for example, Handbook of *Cannabis*, Roger Pertwee, Chapter 1, pages 3 to 15. These cannabinoids can be split into different groups as follows: Phytocannabinoids; Endocannabinoids and Synthetic cannabinoids (which may be novel cannabinoids or synthetically produced phytocannabinoids or endocannabinoids).

"Phytocannabinoids" are cannabinoids that originate from nature and can be found in the *cannabis* plant. The phytocannabinoids can be isolated from plants to produce a highly purified extract or can be reproduced synthetically.

"Highly purified cannabinoids" are defined as cannabinoids that have been extracted from the *cannabis* plant and purified to the extent that other cannabinoids and non-cannabinoid components that are co-extracted with the cannabinoids have been removed, such that the highly purified cannabinoid is greater than or equal to 95% (w/w) pure.

"Synthetic cannabinoids" are compounds that have a cannabinoid or cannabinoid-like structure and are manufactured using chemical means rather than by the plant.

Phytocannabinoids can be obtained as either the neutral (decarboxylated form) or the carboxylic acid form depending on the method used to extract the cannabinoids. For example, it is known that heating the carboxylic acid form will cause most of the carboxylic acid form to decarboxylate into the neutral form.

"Treatment-resistant epilepsy" (TRE) or "intractable epilepsy" is defined as per the ILAE guidance of 2009 as epilepsy that is not adequately controlled by trials of one or more AED.

"Atonic seizures" occur when a person suddenly loses muscle tone so their head or body may go limp. They are also known as drop attacks. In some children, only their head drops suddenly. They can begin in one area or side of the brain (focal onset) or both sides of the brain (generalized onset).

"Tonic seizures" can be generalised onset, affecting both sides of the brain, or they can be focal onset, starting in just one side of the brain. If a tonic seizure starts in both sides of the brain, all muscles tighten and the subject's body goes stiff. If standing, they may fall to the floor, their neck may extend, eyes open wide and roll upwards, whilst their arms may raise upwards and legs stretch or contract. If a tonic seizure starts in one side of the brain muscles tighten in just one area of the body. Tonic seizures usually last less than one minute.

"Focal seizures without impairment" are seizures which originate within networks limited to only one hemisphere where the awareness or responsiveness of the subject is not impaired.

DETAILED DESCRIPTION

Preparation of Highly Purified CBD Extract

The following describes the production of the highly-purified (>95% w/w) cannabidiol extract which has a known and constant composition.

In summary the drug substance used is a liquid carbon dioxide extract of high-CBD containing chemotypes of *Cannabis sativa* L. which had been further purified by a solvent crystallization method to yield CBD. The crystallisation process specifically removes other cannabinoids and plant components to yield greater than or equal to 95% CBD. Although the CBD is highly purified because it is produced from a *cannabis* plant rather than synthetically there is a small number of other cannabinoids which are co-produced and co-extracted with the CBD. Details of these cannabinoids and the quantities in which they are present in the medication are as described in Table A below.

TABLE A

Composition of highly purified CBD extract

| Cannabinoid | Concentration |
|---|---|
| CBD | >95% w/w |
| CBDA | NMT 0.15% w/w |
| CBDV | NMT 1.0% w/w |
| $\Delta^9$ THC | NMT 0.15% w/w |
| CBD-C4 | NMT 0.5% w/w |

>greater than
NMT-not more than

Preparation of Botanically Derived Purified CBD

The following describes the production of the botanically derived purified CBD which comprises greater than or equal to 98% w/w CBD and less than or equal to other cannabinoids was used in the open label, expanded-access program described in Example 1 below.

In summary the drug substance used in the trials is a liquid carbon dioxide extract of high-CBD containing chemotypes of *Cannabis sativa* L. which had been further purified by a solvent crystallization method to yield CBD. The crystallisation process specifically removes other cannabinoids and plant components to yield greater than 95% CBD w/w, typically greater than 98% w/w.

The *Cannabis sativa* L. plants are grown, harvested, and processed to produce a botanical extract (intermediate) and then purified by crystallization to yield the CBD (botanically derived purified CBD).

The plant starting material is referred to as Botanical Raw Material (BRM); the botanical extract is the intermediate; and the active pharmaceutical ingredient (API) is CBD, the drug substance.

All parts of the process are controlled by specifications. The botanical raw material specification is described in Table B and the CBD API is described in Table C.

TABLE B

CBD botanical raw material specification

| Test | Method | Specification |
|---|---|---|
| Identification: | | |
| A | Visual | Complies |
| B | TLC | Corresponds to standard (for CBD & CBDA) |
| C | HPLC/UV | Positive for CBDA |
| Assay: CBDA + CBD | In-house (HPLC/UV) | NLT 90% of assayed cannabinoids by peak area |
| Loss on Drying | Ph.Eur. | NMT 15% |
| Aflatoxin | UKAS method | NMT 4 ppb |
| Microbial: | | |
| TVC | Ph.Eur. | NMT$10^7$ cfu/g |
| Fungi | | NMT$10^5$ cfu/g |
| *E.coli* | | NMT$10^2$ cfu/g |
| Foreign Matter: | Ph.Eur. | NMT 2% |
| Residual Herbicides and Pesticides | Ph.Eur. | Complies |

TABLE C

Specification of an exemplary botanically derived purified CBD preparation

| Test | Test Method | Limits |
|---|---|---|
| Appearance | Visual | Off-white/pale yellow crystals |
| Identification A | HPLC-UV | Retention time of major peak corresponds to certified CBD Reference Standard |
| Identification B | GC-FID/MS | Retention time and mass spectrum of major peak corresponds to certified CBD Reference Standard |
| Identification C | FT-IR | Conforms to reference spectrum for certified CBD Reference Standard |
| Identification D | Melting Point | 65-67° C. |
| Identification E | Specific Optical Rotation | Conforms with certified CBD Reference Standard; −110° to −140° (in 95% ethanol) |
| Total Purity | Calculation | ≥98.0% |
| Chromatographic Purity 1 | HPLC-UV | ≥98.0% |
| Chromatographic Purity 2 | GC-FID/MS | ≥98.0% |
| CBDA | HPLC-UV | NMT 0.15% w/w |
| CBDV | | 0.2-1.0% w/w |
| THC | | 0.01-0.1% w/w |
| CBD-C4 | | 0.3-0.5% w/w |
| Residual Solvents: | | |
| Alkane | GC | NMT 0.5% w/w |
| Ethanol | | NMT 0.5% w/w |
| Residual Water | Karl Fischer | NMT 1.0% w/w |

The purity of the botanically derived purified CBD preparation was greater than or equal to 98%. The botanically derived purified CBD includes THC and other cannabinoids, e.g., CBDA, CBDV, CBD-C1, and CBD-C4.

In some embodiments, the CBD preparation comprises not more than 0.15% THC based on total amount of cannabinoid in the preparation. In some embodiments, the CBD preparation comprises about 0.01% to about 0.1% THC based on total amount of cannabinoid in the preparation. In some embodiments, the CBD preparation comprises about 0.02% to about 0.05% THC based on total amount of cannabinoid in the preparation.

In some embodiments, the CBD preparation comprises about 0.2% to about 1.0% CBDV based on total amount of cannabinoid in the preparation. In some embodiments, the CBD preparation comprises about 0.2% to about 0.8% CBDV based on total amount of cannabinoid in the preparation.

In some embodiments, the CBD preparation comprises about 0.3% to about 0.5% CBD-C4 based on total amount of cannabinoid in the preparation. In some embodiments, the CBD preparation comprises about 0.3% to about 0.4% CBD-C4 based on total amount of cannabinoid in the preparation.

In some embodiments, the CBD preparation comprises about 0.1% to about 0.15% CBD-C1 based on total amount of cannabinoid in the preparation.

Distinct chemotypes of the *Cannabis sativa* L. plant have been produced to maximize the output of the specific chemical constituents, the cannabinoids. Certain chemovars produce predominantly CBD. Only the (−)-trans isomer of CBD is believed to occur naturally. During purification, the stereochemistry of CBD is not affected.

Production of CBD Botanical Drug Substance

An overview of the steps to produce a botanical extract, the intermediate, are as follows:

a) Growing b) Direct drying c) Decarboxylation d) Extraction—using liquid $CO_2$ e) Winterization using ethanol f) Filtration g) Evaporation High CBD chemovars were grown, harvested, dried, baled and stored in a dry room until required. The botanical raw material (BRM) was finely chopped using an Apex mill fitted with a 1 mm screen. The milled BRM was stored in a freezer prior to extraction.

Decarboxylation of CBDA to CBD was carried out using heat. BRM was decarboxylated at 115° C. for 60 minutes.

Extraction was performed using liquid $CO_2$ to produce botanical drug substance (BDS), which was then crystalized to produce the test material. The crude CBD BDS was winterized to refine the extract under standard conditions (2 volumes of ethanol at −20° C. for approximately 50 hours). The precipitated waxes were removed by filtration and the solvent was removed to yield the BDS.

Production of Botanically Derived Purified CBD Preparation

The manufacturing steps to produce the botanically derived purified CBD preparation from BDS were as follows:

a) Crystallization using $C_5$-$C_{12}$ straight chain or branched alkane b) Filtration c) Vacuum drying The BDS produced using the methodology above was dispersed in $C_5$-$C_{12}$ straight chain or branched alkane. The mixture was manually agitated to break up any lumps and the sealed container then placed in a freezer for approximately 48 hours. The crystals were isolated via vacuum filtration, washed with aliquots of cold $C_5$-$C_{12}$ straight chain or branched alkane, and dried under a vacuum of <10 mb at a temperature of 60° C. until dry. The botanically derived purified CBD preparation was stored in a freezer at −20° C. in a pharmaceutical grade stainless steel container, with FDA food grade approved silicone seal and clamps.

Physicochemical Properties of the Botanically Derived Purified CBD

The botanically derived purified CBD used in the clinical trial described in the invention comprises greater than or equal to 98% (w/w) CBD and less than or equal to 2% (w/w) of other cannabinoids. The other cannabinoids present are THC at a concentration of less than or equal to 0.1% (w/w); CBD-C1 at a concentration of less than or equal to 0.15% (w/w); CBDV at a concentration of less than or equal to 0.8% (w/w); and CBD-C4 at a concentration of less than or equal to 0.4% (w/w).

The botanically derived purified CBD used additionally comprises a mixture of both trans-THC and cis-THC. It was found that the ratio of the trans-THC to cis-THC is altered and can be controlled by the processing and purification process, ranging from 3.3:1 (trans-THC:cis-THC) in its unrefined decarboxylated state to 0.8:1 (trans-THC:cis-THC) when highly purified.

Furthermore, the cis-THC found in botanically derived purified CBD is present as a mixture of both the (+)-cis-THC and the (−)-cis-THC isoforms.

Clearly a CBD preparation could be produced synthetically by producing a composition with duplicate components.

Example 1 below describes the use of a botanically derived purified CBD in an open label, expanded-access program to investigate the clinical efficacy and safety of purified pharmaceutical cannabidiol formulation (CBD) in the treatment of Cortical Dysplasia and Cortical Brain Malformation.

Example 1: Clinical Efficacy and Safety of Purified Pharmaceutical Cannabidiol (CBD) in the Treatment of Cortical Dysplasia and Cortical Brain Malformation Study Design Subjects were required to be on one or more AEDs at stable doses for a minimum of two weeks prior to baseline and to have stable vagus nerve stimulation (VNS) settings and ketogenic diet ratios for a minimum of four weeks prior to baseline.

Patients were administered botanically derived purified CBD in a 100 mg/mL sesame oil-based solution at an initial dose of five milligrams per kilogram per day (mg/kg/day) in two divided doses. Dose was then increased weekly by 5 mg/kg/day to a goal of 20 to 25 mg/kg/day.

A maximum dose of 50 mg/kg/day could be utilised for patients who were tolerating the medication but had not achieved seizure control; these patients had further weekly titration by 5 mg/kg/day.

There were 9 patients in this study, and each received CBD for at least 3 months. Modifications were made to concomitant AEDs as per clinical indication.

Seizure frequency, intensity, and duration were recorded by caregivers in a diary during a baseline period of at least 28 days. Changes in seizure frequency relative to baseline were calculated after at least 2 weeks and at defined time-points of treatment.

Statistical Methods:

Patients may be defined as responders if they had more than 50% reduction in seizure frequency compared to baseline. the percent change in seizure frequency was calculated as follows:

$$\%\text{ change seizure frequency} = \frac{(\text{weekly seizure frequency time interval} - (\text{weekly seizure frequency Baseline})}{(\text{weekly seizure frequency Baseline})}$$

The percent change of seizure frequency may be calculated for any time interval where seizure number has been recorded. For the purpose of this example the percent change of seizure frequency for the end of the treatment period was calculated as follows:

$$\%\text{ reduction seizure frequency} = ((\text{weekly seizure frequency Baseline}) - (\text{weekly seizure frequency End})) \times 100$$

Results

Patient Description

The 8 patients enrolled in the open label, expanded-access program were diagnosed with Cortical Dysplasia and Cortical Brain Malformation. These patients experienced several different seizure types including atonic, tonic and focal seizures without impairment and were taking several concomitant AEDs.

The age of patients ranged from 4-16 years, five were male and three were female as detailed in Table 1 below.

TABLE 1

Patient demographics, seizure type and concomitant medication

| Patient Number | Age (years) | Sex | Seizure types | Concomitant AEDs |
|---|---|---|---|---|
| 1 | 15.53 | F | Tonic-clonic, atonic | VPA, CLP, DZP, PMP |
| 2 | 4.45 | M | tonic | RFN, CLN, PHB |
| 3 | 12.00 | M | Tonic, atonic, myoclonic | CLB, LEV |
| 4 | 5.00 | M | Tonic | LTG, OXC, VGB |
| 5 | 4.00 | F | Tonic | TPM, OXC, LCS |
| 6 | 16.18 | M | Focal without impairment | LEV, CLN, OXC, PMP |
| 7 | 12.36 | F | Focal without impairment, focal with impairment | TPM |
| 8 | 12.90 | M | Tonic, atonic | CLB, ETH, OXC |

VPA = valproic acid,
LEV = levetiracetam,
CLB = clobazam,
VGB = vigabatrin,
ZNS = zonisamide,
RFN = rufinamide,
LCS = lacosamide,
TPM = topiramate,
LTG = lamotrigine,
ETH = Ethosuximide,
OXC = Oxcarbarmazepine,
CLR = Clorazepate,
DZP = Diazepam,
PMP = Perampanel,
CLN = Clonazepam,
PHB = Phenobarbital Study Medication and Concomitant Medications All eight patients were titrated up to at least 5 mg/kg/day of CBD, seven patients were titrated up to at least 25 mg/kg/day (#1, 3-8), and two patients were titrated up to 50 mg/kg/day (#4, 5).

The average number of concomitant AEDs at the time of starting CBD was three per patient (range: 1-4, median: 3).

Clinical Changes

The average baseline was 81.8 seizures per week (range: 2.0-280.0 seizures per week median: 24 seizures per week). Tables 2A-H illustrate the seizure frequency for each patient as well as the dose of CBD given.

TABLE 2A

Seizure frequency data for Patient 1
Patient 1

| Time | Seizure Type Tonic-clonic | Seizure Type Atonic | Dose CBD (mg/kg/day) |
|---|---|---|---|
| Baseline | 13.0 | 2.0 | — |
| 2 weeks | 12.0 | 0.0 | 10.0 |
| 4 weeks | 25.0 | 1.0 | 20.0 |
| 8 weeks | 17.0 | 3.0 | 25.0 |
| 12 weeks | 16.0 | 1.0 | 25.0 |

Patient 1 was treated for 12 weeks and experienced a 50% reduction in atonic seizures over the treatment period.

TABLE 2B

Seizure frequency data for Patient 2
Patient 2

| Time | Seizure Type Tonic | Dose CBD (mg/kg/day) |
|---|---|---|
| Baseline | 140.0 | — |
| 12 weeks | 70.0 | 5.0 |

Patient 2 was treated for 12 weeks and experienced a 50% reduction in tonic seizures over the treatment period.

TABLE 2C

Seizure frequency data for Patient 3
Patient 3

| Time | Seizure Type Tonic | Seizure Type Atonic | Seizure Type Myoclonic | Dose CBD (mg/kg/day) |
|---|---|---|---|---|
| Baseline | 20.0 | 24.0 | 4.0 | — |
| 4 weeks | 4.0 | 0.0 | 0.0 | 20.0 |
| 8 weeks | 200.0 | 0.0 | 0.0 | 25.0 |
| 12 weeks | 140.0 | 12.0 | 56.0 | 14.8 |
| 24 weeks | 140.0 | 12.0 | 28.0 | 9.7 |
| 36 weeks | 60.0 | 16.0 | 0.0 | 10.9 |
| 48 weeks | 40.0 | 8.0 | 20.0 | 10.6 |
| 60 weeks | 28.0 | 1.0 | 1.0 | 17.1 |
| 72 weeks | 40.0 | 1.0 | 1.0 | 16.2 |
| 96 weeks | 28.0 | 2.0 | 16.0 | 24.5 |
| 120 weeks | 6.0 | 4.0 | 16.0 | 17.7 |
| 132 weeks | 6.0 | 4.0 | 16.0 | 17.3 |
| 144 weeks | 56.0 | 2.0 | 40.0 | 19.9 |

Patient 3 was treated for 144 weeks and experienced a 91.7% reduction in atonic seizures over the treatment period.

TABLE 2D

Seizure frequency data for Patient 4
Patient 4

| Time | Seizure Type Tonic | Dose CBD (mg/kg/day) |
|---|---|---|
| Baseline | 196.0 | — |
| 4 weeks | 60.0 | 20.0 |
| 8 weeks | 40.0 | 25.0 |
| 12 weeks | 80.0 | 30.0 |
| 24 weeks | 24.0 | 50.0 |
| 36 weeks | 32.0 | 50.0 |
| 48 weeks | 54.0 | 50.0 |
| 60 weeks | 24.0 | 50.0 |
| 72 weeks | 24.0 | 49.0 |
| 84 weeks | 36.0 | 46.0 |
| 96 weeks | 22.0 | 50.0 |
| 120 weeks | 16.0 | 42.6 |
| 132 weeks | 36.0 | 49.8 |

Patient 4 was treated for 132 weeks and experienced an 81.6% reduction in tonic seizures over the treatment period.

TABLE 2E

Seizure frequency data for Patient 5
Patient 5

| Time | Seizure Type Tonic | Dose CBD (mg/kg/day) |
|---|---|---|
| Baseline | 4.0 | — |
| 4 weeks | 3.2 | 20.0 |
| 8 weeks | 11.0 | 35.0 |
| 12 weeks | 1.0 | 50.0 |
| 24 weeks | 0.0 | 50.0 |
| 36 weeks | 0.0 | 47.0 |
| 48 weeks | 1.0 | 46.0 |
| 60 weeks | 1.0 | 49.0 |
| 72 weeks | 0.0 | 50.0 |
| 84 weeks | 0.0 | 50.0 |
| 96 weeks | 0.0 | 49.7 |
| 108 weeks | 0.0 | 49.7 |
| 132 weeks | 0.0 | 49.1 |
| 144 weeks | 0.0 | 50.0 |

Patient 5 was treated for 144 weeks and experienced a 100% reduction in tonic seizures over the treatment period.

TABLE 2F

Seizure frequency data for Patient 6
Patient 6

| Time | Seizure Type Focal without impairment | Dose CBD (mg/kg/day) |
|---|---|---|
| Baseline | 20.0 | — |
| 4 weeks | 8.0 | 25.0 |
| 8 weeks | 0.0 | 25.0 |
| 16 weeks | 4.0 | 25.0 |
| 24 weeks | 2.0 | 25.0 |

Patient 6 was treated for 24 weeks and experienced a 90% reduction in focal seizures without impairment over the treatment period.

TABLE 2G

| Seizure frequency data for Patient 7 Patient 7 | | | |
|---|---|---|---|
| | Seizure Type | | Dose CBD |
| Time | Focal without impairment | Focal with impairment | (mg/kg/day) |
| Baseline | 233.0 | 49.0 | — |
| 2 weeks | 182.0 | 22.0 | 10.0 |
| 4 weeks | 62.0 | 26.0 | 20.0 |
| 8 weeks | 125.0 | 35.0 | 25.0 |
| 12 weeks | 112.0 | 40.0 | 25.0 |
| 16 weeks | 93.3 | 66.7 | 25.0 |
| 24 weeks | 96.8 | 62.4 | 25.0 |
| 36 weeks | 39.7 | 94.8 | 20.0 |
| 48 weeks | 92.9 | 62.5 | 20.0 |
| 60 weeks | 141.2 | 72.8 | 20.0 |
| 72 weeks | 139.4 | 179.7 | 20.0 |

Patient 7 was treated for 72 weeks and experienced a 40.2% reduction in focal seizures without impairment over the treatment period.

TABLE 2H

| Seizure frequency data for Patient 8 Patient 8 | | | |
|---|---|---|---|
| | Seizure Type | | Dose CBD |
| Time | Tonic | Atonic | (mg/kg/day) |
| Baseline | 280.0 | 80.0 | — |
| 4 weeks | 6.0 | — | 20.0 |
| 8 weeks | 5.0 | — | 25.0 |
| 12 weeks | 60.0 | 12.0 | 25.0 |
| 16 weeks | 56.0 | 24.0 | 25.0 |
| 24 weeks | 32.0 | 4.0 | 25.0 |
| 36 weeks | 896.0 | 4.0 | 10.0 |

Patient 8 was treated for 36 weeks and experienced a 95.0% reduction in atonic seizures over the treatment period.

Overall, patients reported reductions of 40.2-100.0% in seizures over period of treatment with CBD.

CBD was effective in reducing the frequency of the following seizure types: atonic, tonic and focal without impairment. Significantly, one patient became seizure free of tonic seizures after 12 months of CBD treatment.

CONCLUSIONS

These data indicate that CBD was able to significantly reduce the number of seizures associated with Cortical Dysplasia and Cortical Brain Malformation. Clearly the treatment is of significant benefit in this difficult to treat epilepsy syndrome given the high response rate experienced in all patients.

Of interest is that a patient with tonic seizures (patient 5) obtained significant benefit whereby the patient was completely seizure free after 12 months of treatment.

In conclusion, this study signifies the use of CBD for treatment of seizures associated with Cortical Dysplasia and Cortical Brain Malformation. Seizure types include atonic, tonic, and focal seizures without impairment for which seizure frequency rates decreased by significant rates, by 40.2-100.0%.

REFERENCES

1. Kabat & Krol. (2012) "Focal cortical dysplasia—review." Polish Journal of Radiology.
2. Leventer. (2008) "Malformations of cortical development and epilepsy." Dialogues in Clinical Neuroscience V.10 (1)
3. https://www.dailyrecord.co.uk/news/local-news/we-it-family-overioyed-cannabis-13859745
4. Garcia-Rincón et al. (2019) "Contribution of Altered Endocannabinoid System to Overactive mTORC1 Signaling in Focal Cortical Dysplasia." Frontiers in Pharmacology.
5. Szaflarski et al. (2018) "Long-term safety and treatment effects of cannabidiol in children and adults with treatment-resistant epilepsies." Epilepsia, 2018, 59; 1540-1548
6. Laux et al. (2019) "Long-term safety and efficacy of cannabidiol in children and adults with treatment resistant Lennox-Gastaut syndrome or Dravet syndrome: Expanded access program results." Epilepsy Research, 2019, 154; 13-20
7. Crippa et al. (2016) "9-THC Intoxication by Cannabidiol-Enriched *Cannabis* Extract in Two Children with Refractory Epilepsy: Full Remission after Switching to Purified Cannabidiol." Front Pharmacol, 2016, 7; 359
8. Longley (2014) "Arizona Superior Court Helps 5-Year-Old Zander Welton With Cannabis Extract Ruling." https://www.medicaljane.com/2014/03/24/arizona-supreme-court-helps-5-year-old-zander-welton-with-cannabis-extract-rulinq/#:~:text=PHOENIX %2C %20AZ %20% E2%80%93%20Judge %20Katherine %20Cooper, th eir %20severe %20seizures %20 from %20epilepsy.
9. Mohney (2013) "Parents file suit to allow son to take marijuana extract." https://abcnews.go.com/Health/parents-file-suit-son-medicinal-marijuana-extract/story?id=20740614

The invention claimed is:

1. A method of treating seizures associated with Cortical Brain Malformation, wherein the seizures associated with Cortical Brain Malformation are atonic, tonic, and focal without impairment seizures comprising administering a cannabidiol (CBD) drug substance, wherein the CBD drug substance comprises greater than 95% (w/w) CBD and not more than 0.15% (w/w) tetrahydrocannabinol (THC), wherein the CBD drug substance provides a dose of CBD in the range of 5 mg/kg/day to 50 mg/kg/day.

2. The method of claim 1, wherein the CBD drug substance comprises greater than or equal to 98% (w/w) CBD and less than or equal to 2% (w/w) other cannabinoids, wherein the less than or equal to 2% (w/w) other cannabinoids comprise the cannabinoids tetrahydrocannabinol (THC); cannabidiol-C1 (CBD-C1); cannabidivarin (CBDV); and cannabidiol-C4 (CBD-C4), and wherein the THC is present as a mixture of trans-THC and cis-THC.

3. The method of claim 1, wherein the CBD preparation is used in combination with one or more concomitant anti-epileptic drugs (AED).

4. The method of claim 3, wherein the one or more AED is selected from the group consisting of: valproic acid, levetiracetam, clobazam, vigabatrin, zonisamide, rufinamide, lacosamide, topiramate and lamotrigine.

5. The method of claim 1, wherein the CBD is present is isolated from *cannabis* plant material.

6. The method of claim 1, wherein at least a portion of at least one of the cannabinoids present in the CBD preparation is isolated from *cannabis* plant material.

7. The method of claim 1, wherein the CBD is present as a synthetic drug substance.

8. The method of claim 7, wherein at least a portion of at least one of the cannabinoids present in the CBD drug substance preparation is prepared synthetically.

9. The method of claim 1, wherein the dose of CBD is greater than 5 mg/kg/day.

10. The method of claim 1 wherein the dose of CBD is 20 mg/kg/day.

11. The method of claim 1, wherein the dose of CBD is 25 mg/kg/day.

12. The method of claim 1, wherein the dose of CBD is 50 mg/kg/day.

13. The method of claim 1, wherein the cortical brain malformation is cortical dysplasia.

* * * * *